US00PP14972P2

(12) United States Plant Patent
Zary

(10) Patent No.: US PP14,972 P2
(45) Date of Patent: Jun. 29, 2004

(54) FLORIBUNDA ROSE PLANT NAMED 'JACAROBE'

(50) Latin Name: *Rosa hybrida*
Varietal Denomination: JACarobe

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/300,860

(22) Filed: Nov. 19, 2002

(51) Int. Cl.[7] ..... A01H 5/00
(52) U.S. Cl. ..... Plt./145
(58) Field of Search ..... Plt./145, 141, 104, Plt./134

*Primary Examiner*—Anne Marie Grunberg
*Assistant Examiner*—June Hwu
(74) *Attorney, Agent, or Firm*—Klarquist Sparkman LLP

(57) ABSTRACT

Floribanda rose plant having strong fragrance; large flower size; dark, glossy, healthy foliage; vigorous growth; and deep, lasting, yellow flower color.

1 Drawing Sheet

Genus and Species: *Rosa hybrida.*
Variety Denomination 'JACarobe'.

SUMMARY OF THE INVENTION

The present invention relates to a new and distinct variety of floribunda rose plant named 'JACarobe' which was originated by me by crossing the variety 'AROfres,' (unpatented) with the variety 'HARroony,' U.S. Plant Pat. No. 5,582.

BACKGROUND OF THE INVENTION

The primary objective of this breeding was to produce a new rose variety having strong vigorous growth and healthy foliage of the yellow floribunda female parent combined with the larger flower, high petal count and strong fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong fragrance;
2. Large flower size;
3. Dark, glossy, healthy foliage;
4. Vigorous growth; and
5. Deep, lasting, yellow flower color.

Asexual reproduction of this new variety by budding, as performed at Wasco, Calif., shows that the foregoing and all other characteristics and distinctions come true to form and are established and transmitted through succeeding propagations.

Comparison with Parents

'JACarobe' differs from the female parent in that the female parent has no fragrance, is more compact and has smaller flowers. 'JACarobe' differs from the male parent in that the male parent has a different flower color, larger foliage and larger flower size.

Comparison with Similar Variety

Differs from other yellow floribundas in flower fragrance, the lasting quality of the yellow color and its excellent, healthy foliage. It differs from the variety 'JACjem' (U.S. Plant Pat. No. 5,001) in that 'JACarobe's' blooms have fewer petals, a much stronger fragrance and larger size.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'AROfres' (Unpatented).
*Pollen parent.*—'HARoony' (U.S. Plant Pat. No. 5,582).

FLOWER

Observations made from plants beginning at 3 years of age grown in a garden environment at Somis, Calif. May 2001–May 2002.

Blooming habit: Continuous.
Bud:
*Size.*—About 3 cm long and 2 cm in diameter when the petals start to unfurl.
*Form.*—The bud form is long, pointed ovoid.
*Color.*—When sepals first divide, bud color is Yellow Group 6C. When half blown, the upper sides of the petals are Yellow Group 6C; and the lower sides of the petals are Yellow Group 6D.

*Sepals.*—Color: Upper surface: Green Group 138B. Lower surface: Yellow-Green Group 146B. Length: 35–40 mm. Width: 9–10 mm. Shape: Subulate. Surface texture: Upper surface: Hoary. Lower surface: Glandular. There are three normally appendaged sepals. There are two unappendaged sepals with hairy edges.

*Receptacle.*—Color: Yellow-Green Group 146B. Shape: Funnel. Size: Medium, about 7 mm long×11 mm wide. Surface: Smooth.

*Peduncle.*—Length: Medium, averaging about 60–70 mm. Surface: Rough, prickly and glandular. Color: Yellow-Green Group 146B to C. Strength: Stiff, erect.

Bloom:

*Size.*—Medium. Average open diameter is about 10–11 cm.

*Borne.*—Several together in flat clusters of 3–5 blooms.

*Stems.*—Strength: Strong. Average length is about 30–40 cm, diameter 6–7 mm.

*Form.*—When first open: High centered. Permanence: Flattens, outer petals curl back.

*Petalage.*—Number of petals under normal conditions: 20.

*Color.*—The upper sides of the petals are Yellow Group 6C. The reverse sides of the petals are Yellow Group 6D. The major color on the upper side is Yellow Group 6C.

*Variegations.*—None.

*Discoloration.*—The general tonality at the end of the first day: No change. At the end of the third day: No change. By day 5 or 6 there is a general fading to Yellow Group 6D.

*Fragrance.*—Strong, spicy.

Petals:

*Size.*—Width: 4 cm. Length: 5 cm.

*Texture.*—Thick.

*Surface.*—Smooth.

*Shape.*—Orbicular to obovate.

*Margin.*—Entire. Apex shape: Mucronulate. Base shape: Cuneate.

*Form.*—Tips slightly recurved.

*Arrangement.*—Imbricated.

*Petaloids.*—Number: None.

*Persistence.*—Petals drop off cleanly before drying.

*Lastingness.*—On the plant: Fair (about 5 or 6 days). As a cut flower: Fair (about 6 or 7 days).

Reproductive parts:

*Stamens.*—Number: 130–150. Length: 7–8 mm. Anthers: Length: 2 mm. Color: Yellow-Orange Group 16B. Arrangement: Regular around styles. Filaments: Color: Yellow-Orange Group 16B. Length: 5–6 mm. Pollen: Color: Yellow-Orange Group 22A.

*Pistils.*—Number: 80–90. Length: 7–8 mm. Styles: Color: Greyed-Purple Group 183D on the upper third, then White Group 155B. Length: 6–7 mm. Stigmas: Color: Greyed-Yellow Group 161D. Length: 1 mm.

*Hips.*—None observed.

PLANT

*Form.*—Bush.

*Growth.*—Vigorous, upright and branching.

*Mature plant.*—Height: 120 cm at 2 years of age. Width: 80 cm.

*Rootstock.*—Dr. Huey.

Foliage: Number of leaflets on normal mid-stem leaves: 5 or 7.

*Size.*—Medium (12 cm long×10 cm wide).

*Quantity.*—Abundant.

*Color.*—New foliage: Upper side: Greyed-Orange Group 173A with Yellow-Green Group 144B along the mid rib. Lower side: Same as upper. Old foliage: Upper side: Green Group 136A. Lower side: Green Group 137C.

Leaflets:

*Size.*—About 45 mm long×40 mm wide.

*Shape.*—Broadly oval.

*Base shape.*—Rounded.

*Apex shape.*—Cuspidate.

*Texture.*—Coriaceous, glossy, lustrous.

*Edge.*—Serrated.

*Serration.*—Single, small.

*Petiole.*—Color: Yellow-Green Group 146C.

*Petiole rachis.*—Color: Yellow-Green Group 146C. Underside: Rough with prickles and glands.

*Auricle shape.*—None present.

*Stipules.*—Serrated (about 20–25 mm.) Shape: Adnate and parallel. Color: Upper surface: Green Group 136A. Lower surface: Green Group 137C.

*Disease resistance.*—Resistant to mildew and rust and susceptible to blackspot under normal growing conditions.

*Pest resistance.*—Not observed.

*Vein color.*—Green Group 137C.

*Venation pattern.*—Reticulate.

Wood:

*New wood.*—Color: Yellow-Green Group 146B. Bark: Smooth.

*Old wood.*—Color: Green Group 137C. Bark: Smooth.

Prickles:

*Quantity.*—On main canes from base: Ordinary (15 per 15 cm). On laterals from main canes: Ordinary.

*Form.*—Straight.

*Length.*—10–12 mm.

*Color when young.*—Greyed-Purple Group 185D.

*Color when mature.*—Greyed-Yellow Group 161C.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its strong fragrance; large flower size; dark, glossy, healthy foliage; vigorous growth; and deep, lasting, yellow flower color.

* * * * *

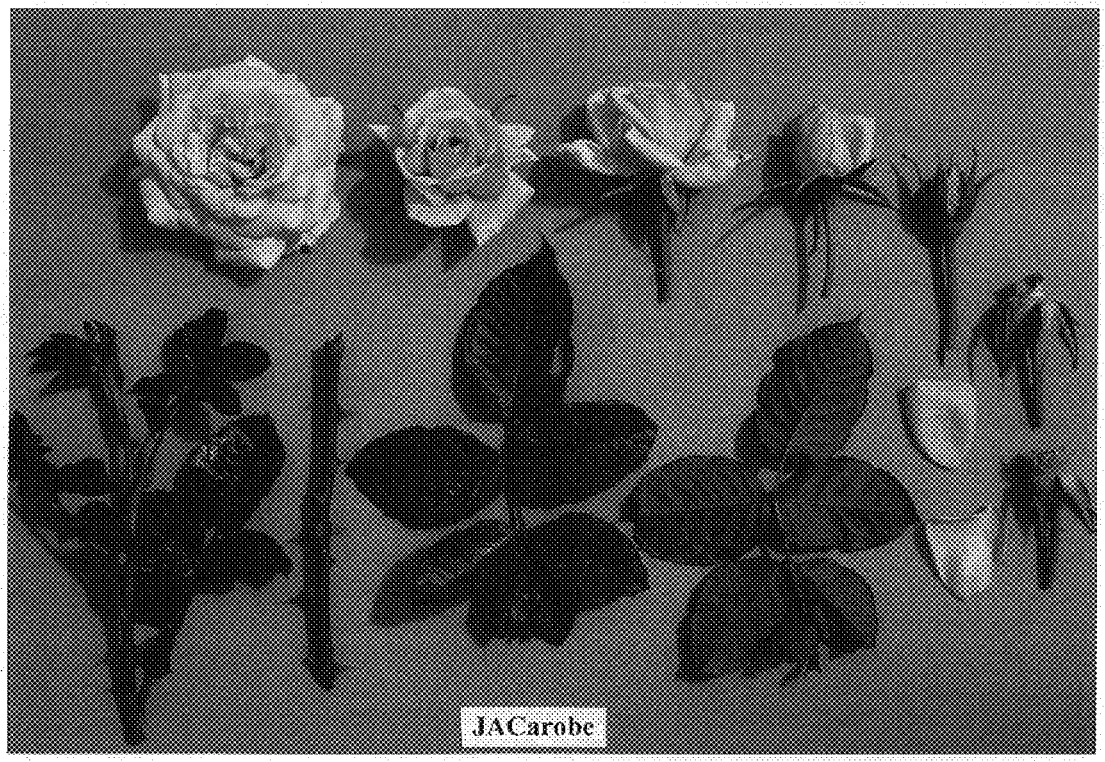
JACarobe